(12) United States Patent
Allman et al.

(10) Patent No.: US 10,179,180 B2
(45) Date of Patent: Jan. 15, 2019

(54) LOCAL THERMAL ACTUATION OF MATERIAL SURFACES VIA MICRO- AND NANOWIRE HEATING FOR THE PREVENTION OF CELLULAR ATTACHMENT AND BIOLOGICAL FOULING

(71) Applicant: UT-Battelle, LLC, Oak Ridge, TN (US)

(72) Inventors: Steve L. Allman, Knoxville, TN (US); Mitchel J Doktycz, Knoxville, TN (US); Scott T Retterer, Knoxville, TN (US); David P. Allison, Lenoir City, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 133 days.

(21) Appl. No.: 14/451,967

(22) Filed: Aug. 5, 2014

(65) Prior Publication Data
US 2015/0044092 A1    Feb. 12, 2015

Related U.S. Application Data

(60) Provisional application No. 61/862,604, filed on Aug. 6, 2013.

(51) Int. Cl.
*A61L 2/03*      (2006.01)
*A61L 27/44*     (2006.01)
(Continued)

(52) U.S. Cl.
CPC ............... *A61L 2/03* (2013.01); *A61L 27/34* (2013.01); *A61L 27/443* (2013.01);
(Continued)

(58) Field of Classification Search
CPC ........................................................ A61L 2/03
(Continued)

(56) References Cited

U.S. PATENT DOCUMENTS

| 2005/0038498 A1 | 2/2005 | Dubrow |
| 2007/0299518 A1 | 12/2007 | Ruane |

(Continued)

FOREIGN PATENT DOCUMENTS

| BY | 13256 | 6/2010 |
| CA | 2712832 | 8/2009 |

(Continued)

OTHER PUBLICATIONS

Park et al., Towards the silicon nanowire-based sensor for intracellular biochemical detection, 2006, Biosensors and bioelectronics, vol. 22, pp. 2065-2070.*

(Continued)

*Primary Examiner* — Kevin Joyner
*Assistant Examiner* — Holly M Mull
(74) *Attorney, Agent, or Firm* — Scully Scott Murphy & Presser

(57) ABSTRACT

The invention relates in various embodiments to a composite useful as e.g. a medical implant device, and a method of treating fouling, including biofouling as may occur on an implant. The composite comprises a matrix phase and a patterned phase that comprises an energetically activatable wire intermixed with the matrix phase, the wire when energetically activated, which includes thermal activation, causes modification of at least a portion of the matrix phase to treat fouling that might otherwise occur. The method of treating biofouling may be practiced on a patent while the medical implant of the invention is in situ.

17 Claims, 2 Drawing Sheets

(51) Int. Cl.
*A61L 27/50* (2006.01)
*A61L 29/12* (2006.01)
*A61L 29/14* (2006.01)
*A61L 27/48* (2006.01)
*A61L 31/12* (2006.01)
*A61L 31/14* (2006.01)
*A61L 27/34* (2006.01)
*A61L 29/08* (2006.01)
*B82Y 30/00* (2011.01)
*B82Y 40/00* (2011.01)

(52) U.S. Cl.
CPC ............ *A61L 27/446* (2013.01); *A61L 27/48* (2013.01); *A61L 29/085* (2013.01); *A61L 29/126* (2013.01); *A61L 31/126* (2013.01); *A61L 31/128* (2013.01); *A61L 31/129* (2013.01); *A61L 31/14* (2013.01); *Y10T 428/31507* (2015.04); *Y10T 428/31551* (2015.04); *Y10T 428/31605* (2015.04); *Y10T 428/31663* (2015.04); *Y10T 428/31681* (2015.04); *Y10T 428/31692* (2015.04); *Y10T 428/31721* (2015.04); *Y10T 428/31725* (2015.04); *Y10T 428/31739* (2015.04); *Y10T 428/31826* (2015.04); *Y10T 428/31938* (2015.04)

(58) Field of Classification Search
USPC .......................................................... 422/23
See application file for complete search history.

(56) References Cited

U.S. PATENT DOCUMENTS

| | | |
|---|---|---|
| 2008/0181931 A1 | 7/2008 | Qiu |
| 2009/0093879 A1* | 4/2009 | Wawro .................. A61F 2/0077 623/11.11 |
| 2009/0117045 A1 | 5/2009 | Katti |
| 2010/0050793 A1* | 3/2010 | Ahn ........................ A61B 5/441 73/866 |
| 2010/0056894 A1 | 3/2010 | Cote |
| 2010/0331978 A1 | 12/2010 | Stromme |
| 2012/0241632 A1 | 9/2012 | Cordaro |
| 2014/0330337 A1* | 11/2014 | Linke .................. A61N 1/3787 607/45 |
| 2016/0066789 A1* | 3/2016 | Rogers ...................... A61N 1/05 604/20 |

FOREIGN PATENT DOCUMENTS

| | | |
|---|---|---|
| RU | 2 465 288 | 7/2009 |
| WO | WO 2006/098872 | 9/2006 |
| WO | WO 2006/098872 A2 | 9/2006 |
| WO | WO 2007/078304 | 7/2007 |
| WO | WO 2007/078304 A2 | 7/2007 |
| WO | WO 2007/098050 | 8/2007 |
| WO | WO 2010/068985 | 6/2010 |
| WO | WO 2010/068985 A1 | 6/2010 |
| WO | WO 2012/154535 | 11/2012 |

OTHER PUBLICATIONS

Guo et al., An effective lift-off method for patterning high-density gold interconnects on an elastic substrate, Dec. 2010, NIH, pp. 1-20 (Year: 2010).*

Axisa et al., Elastic and conformable electronic circuits and assemblies using MID in polymer, 2007, IEEE, pp. 280-286 (Year: 2007).*

Bongartz T, et al., "Incidence and Risk Factors of Prosthetic Joint Infection After Total Hip and Knee Replacement in Patients with Rheumatoid Arthritis", (2008) Arthritis and Rheumatism 59(12), 1713-1720.

Maki, D.G. Engineering Out the Risk of Infection with Urinary Catheters, (2001) Energ. Infect. Dis 7(2): 1-6.

Pittet, et al., "Infection in Breast Implants", (2005) Lancet Infect. Dis. 5:94-106.

Pagani J.L., "Management of Catheter Related Infections" (2008) Expert Rev. Anti. Infect Ther. 6(1): 31-37.

Extended European Search Report dated Nov. 18, 2014 received from EP Application No. 12782393.8.

International Search Report dated Sep. 13, 2012 issued in PCT/US2012/036468.

International Search Report dated Nov. 27, 2014 issued in PCT/US2014/049557.

Maki, D.G. Engineering Out the Risk of Infection with Urinary Catheters, (2001) Enger. Infect. Dis 7(2): 1-6.

* cited by examiner

LOCAL THERMAL ACTUATION OF MATERIAL SURFACES VIA MICRO- AND NANOWIRE HEATING FOR THE PREVENTION OF CELLULAR ATTACHMENT AND BIOLOGICAL FOULING

CROSS-REFERENCE TO RELATED APPLICATIONS

This application claims priority to U.S. Provisional Application No. 61/862,604, filed Aug. 6, 2013, which is incorporated herein in its entirety.

STATEMENT REGARDING FEDERALLY SPONSORED RESEARCH OR DEVELOPMENT

This invention was made with government support under Contract No. DE-AC05-00OR22725 awarded by the United States Department of Energy. The government has certain rights in the invention.

FIELD OF THE INVENTION

The present invention relates to structures, such as composites, and methods useful for the treatment of fouled surfaces, including e.g. the surfaces of medical implants and the treatment of same to, among other things, resist biological fouling and infection associated, e.g., with cellular attachment, early stage protein adsorption and the like.

BACKGROUND OF THE INVENTION

Medical implants, including devices such as catheters and the like, are prone to contamination by bacteria and other microbial species such as yeast and fungi. While various techniques are known to sterilize these devices prior to implantation, there are few methods of remediating contamination that occurs post implantation. For example, the implanted devices can be removed and replaced; but this type of intervention is stressful to the patient, has the potential of creating other risks, and can be expensive. In lieu of removal and replacement, treatment of bacterial infections of implanted devices by administering antibiotics is known. Such antibiotic therapy, however, often proves difficult, even ineffective, due to microbial drug resistance and/or the formation of a biofilm related to the infection that resists antibiotic penetration. In addition, antibiotic treatments of this sort can be expensive, and long term with attendant consequences to patient health. There is thus a need for an improved device and method for resisting contamination as aforesaid.

SUMMARY OF THE INVENTION

In one aspect, the invention relates to a structure and method to prevent and treat fouling, including biological fouling. In one embodiment, the invention is a composite comprised of a matrix phase comprised, e.g. of a polymer, which can further comprise a patterned phase comprised of an energetically activatable wire which, when activated, causes modification of the composite effective to treat fouling, including surface fouling, by e.g. causing mechanical motion and/or changes in physical and/or chemical properties of the surface sufficient to obstruct and/or disrupt fouling films that may form. The patterned wire in this regard includes one or more wires, such as one or more nanowires and/or one or more microwires which can be the same or of different sizes, and be of the same or different materials of construction, and combinations thereof, which wire is comprised of conductive materials that are patterned or formed by e.g. lithographic means, other physical implantation, and the like, and that are intermixed, e.g. embedded in and/or integral to the matrix phase as herein described. In one aspect, the subject wire is configured to have a periodicity at least commensurate with cellular scale, preferably sub-cellular scale. In one practice, the composite comprises a medical implant device. In one practice in this regard, the medical implant device is preferably comprised of a polymer material patterned with one or more wires as foresaid; in one embodiment in this regard, the polymer material that the implant device is comprised of is over-coated to effectively embed the one or more wires; in one aspect of this practice, the over-coat is comprised of a second polymer material which can be the same or different from the polymer material that the implant device is otherwise comprised of. In another aspect, the wire is patterned onto polymer sheets which can then be configured into complex structures such as mesh nets, coils, post arrays and the like, which can then be attached or otherwise incorporated to the surface(s) of various medical implant devices.

In one embodiment, the implant device has means to connect the patterned wire to an electrical current, such as from an external power source or current as generated by exposure to an electromagnetic field under conditions effective to create electric time varying and/or pulse varying current as contemplated herein. In one practice, a time varying application of electrical current to the wire causes thermal actuation of at least a portion of the surface of the polymer matrix material whereby rapidly alternating ohmic heating and cooling occurs effective to cause dynamic chemical and/or physical changes, such as mechanical motion, in the surface, such as changes in temperature, expansion and/or elasticity. In one practice, the current is cycled so as to produce dynamic surface changes sufficient to resist biological fouling of the surface; for example, the dynamically changing local topography and/or elasticity of the surface resists early stage protein adsorption and/or cellular attachment typically associated with infection and biofilm formation. In another practice, the invention relates to a method of resisting biofouling by way of the subject medical implant device. In one embodiment of the method, thermal actuation and attendant resistance to biofouling occurs in situ, post implantation of the device, thus eliminating the need to remove the implant from the patient.

In various embodiments, the invention can be a medical implant device, such as, without limitation, a catheter, a shunt, a stent, an orthopedic implant such as an artificial joint, a prosthetic device, a breast implant, dental implant, and the like. In one practice, the implant device can be in the form of a sheet or tube insert useful, e.g. to line the lumen of a conventional catheter or shunt; in another practice, the implant device can be in the form of a thin sheet configured to cover the outer surface of a conventional implant; in another practice, the implant of the invention can be in the form of multiple sheets comprising the wire heaters embedded in respective patterns to form active surfaces that can be configured into multi-dimensional, e.g. two dimensional, architectures such as mesh nets, coils, post arrays, and the like, that can be optimized and attached or otherwise incorporated into medical implant devices having more complex surfaces, such as figuring coatings for prosthetic devices or implants with complex three dimensional surfaces.

DETAILED DESCRIPTION OF THE INVENTION

Figure 1:
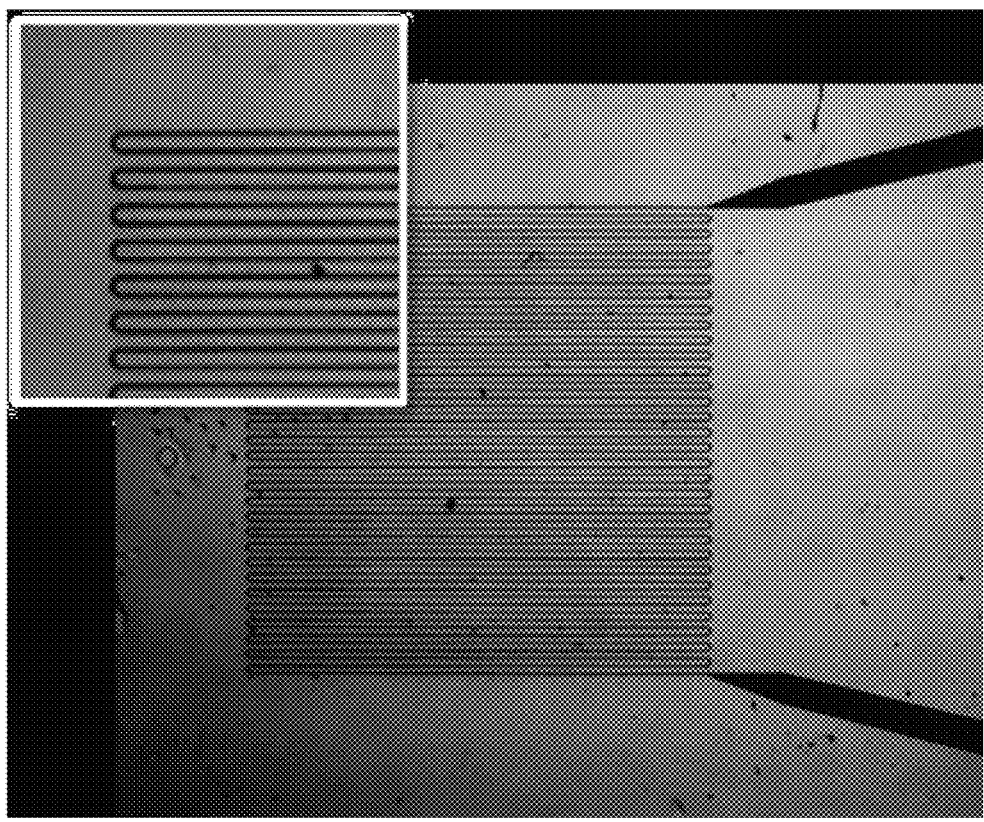
FIG. 1 depicts an aspect of an embodiment of the implant of the invention showing a microwire in a sinuous configuration of reduced periodicity wherein the wire is comprised of a single, continuous wire onto which an over-coated polymer material can be applied.

Detailed embodiments of the present invention are described herein; however, it is to be understood that the disclosed embodiments are merely illustrative of the devices and methods of the invention that may be embodied in various forms. In addition, each of the examples given in connection with the various embodiments are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the compositions, structures and methods disclosed herein. References in the specification to an "embodiment" and the like indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

In one embodiment the invention relates to a composite comprising a matrix phase of a first material composition; and a patterned phase comprising an energetically activatable wire of a second material composition intermixed with the matrix phase of the first material composition, the wire when energetically activated causing modification of the matrix phase to treat fouling of the composite. The term "intermixed" as used herein includes, without limitation, configurations wherein the patterned wire is embedded in, integral to and/or otherwise a part of the patterned phase and the composite. In another embodiment, the invention is to a coated structure comprising a matrix phase of a first material of composition, the matrix phase having a surface; and a coating of an energetically activatable wire of a second material of composition on the surface of the matrix phase, wherein when activated the wire modifies a chemical property, or a physical property, or a combination of a chemical and physical property of the surface of the matrix phase to treat fouling of the coated structure. In another embodiment, the invention is to a medical implant device comprising a matrix phase comprised of a polymer; and a patterned phase comprising at least one energetically activatable wire comprising a nanowire, a microwire or combinations thereof, which wire is comprised of a metal or metal oxide selected, without limitation, from the group consisting of gold, silver, copper, iron, palladium, platinum, and combinations thereof as well as carbon and conducting organic polymers or combinations thereof, said wire lithographically defined within the patterned phase and intermixed with the matrix phase, the wire when energetically activated causing modification of the matrix phase to treat fouling of the medical implant device. Implant devices contemplated comprise, without limitation, those known in the art for human and animal use, in particular, those implanted temporarily and, more preferably, for extended periods of time, and/or implanted for various reasons, such as medical tests, drug treatments and delivery, cosmetic applications, long term corrective measures, and the like.

By way of example only, representative implant devices of the invention include: catheters, including vascular catheters as used e.g. in kidney dialysis, or as used to introduce or extract materials, medications, nourishment, liquids, drugs, blood and the like to patients over extended periods of time, and including urinary catheters used to both monitor and assure urinary output; shunts, including those inserted into patients to move liquids from one body part to another, e.g. ventriculoperitoneal shunts used to relieve intracranial pressure by moving excess cerebrospinal fluid from the brain, and including tubes placed in the ears of children to move fluid and relieve pressure; breast implants and other cosmetic devices; orthopedic devices, such as artificial joints, including artificial knees, shoulders, hips, ankles and the like; dental implants; stents; and the like.

In one practice, the present invention is to a method of treating fouling. As used herein, the term "treating" and the like includes, without limitation, resisting, disrupting, obstructing and/or preventing of the attachment and growth of fouling materials, especially of biological fouling as caused e.g. by microorganisms on the surface of a device, such as the surface of a medical implant device that is subject to thermal actuation as herein described. In one practice, the invention is to a method of treating biological fouling comprising providing a structure comprising a matrix phase and a patterned phase comprising an energetically activatable wire intermixed with the matrix phase, and energetically activating the wire to cause a physical change in the structure effective to treat the biological fouling. In one practice, the implant is in situ in a patient in need of such treatment. As used herein, the term "biological fouling" and the like denotes, e.g., the deposition or growth of microorganisms on the surface of a medical implant. In one example, biofouling of the surface of the medical implant device includes microbial interactions with the surface of the medical implant device that can progress to form stable biofilms that can lead to medical complications, such as infection in the subject receiving the medical implant. In addition to biofouling and also included in that term as used herein, the present invention also relates to organic, inorganic and particle fouling. Inorganic fouling may include the deposition of an inorganic material, such as silt, clay or humic particles, whereas organic fouling may include deposition of organic materials, such as fat, oil, proteins, or biomolecules. Particle fouling may include precipitation of inorganic crystals.

As used herein, the term "wire" intends embodiments wherein one continuous wire is patterned, e.g. embedded and configured effective as herein described to provide thermal actuation of at least a portion of the surface of the implant device, including mechanical surface motion; and intends embodiments wherein multiple wires of the same or different materials of construction and/or the same or different sizing and/or periodicity are so patterned and so configured. In one practice, the wire is a microscale wire, a nanoscale wire, or a combination of both. Serviceable materials of construction for the wire heater include, e.g., those materials known in the art to provide ohmic (resistive) heating. Representative examples of such materials useful for the wire heater of the invention include, without limitation: metals or metal oxides that are composed of gold, silver, copper, iron, palladium, platinum, and combinations thereof as well as carbon and conducting organic polymers.

In one embodiment, the invention is directed to a medical implant device that is comprised of a matrix phase material comprised, e.g. of a polymer or combination of polymers, that further comprises a patterned phase of at least one energetically activatable wire. The implant device of the invention can be either constructed in whole or in part from the polymeric matrix material and/or constructed of other materials known in the art for such purposes which are then coated or lined with the polymer material. Representative polymer materials suitable for the matrix phase include those known in the art and biocompatible as needed for the use setting contemplated. Without limitation, such polymer matrix materials include: polyesters, including fluoropolymers, such as those in the Teflon family, e.g. polytetrafluoroethylene (PTFE); polyurethanes, including e.g. polycarbonate-based polyurethanes, polyether-based polyurethanes and polyester-based polyurethanes; polyamides and polyamide block copolymers, including e.g. nylon and its various block copolymers; polyolefins, such as high-density polyethylene (HDPE); silicones; latexes; polyvinyl chlorides (PVC); polyimides; polyetheretherketone; and combinations thereof.

In one practice, the patterned wire is lithographically defined using techniques known in the art, such as photolithography and electron beam lithography. In one embodiment, known lithographic techniques are used to create a polymer resist mask or template on which a metallic material can be deposited, e.g. by evaporation. The resist mask is then removed, e.g. with a suitable solvent, and the evaporated metal is left behind in areas previously unprotected by the resist mask. In one practice, wire patterns, including long continuous lines, with a cross section defined by the width of the two dimensional resist mask and thickness of the evaporated metal film, can be created. As known in the art, the resistance of the wire is a function of the wire cross section, length, and metal resistivity. The thermal energy (TE) emitted by a wire is known to be equal to the square of the current (I) passing through the wire multiplied by the resistance (R), or $TE=I^2R$. In a preferred practice, the patterned wire has a periodicity, as known in the art, that is reduced to be at or near the cellular scale, including preferably the sub-cellular scale, including without limitation, a range of about 10 nanometers to about 100 microns, the latter preferably being about 10 microns or less. In one practice, the patterned wire can be lithographically defined or physically implanted otherwise to provide thermal actuation at different length scales, e.g. nanometer to centimeter range. FIG. 1 shows an embodiment of the invention wherein a single continuous patterned wire has been lithographically applied in a sinuous pattern onto a polymer matrix material; the periodicity shown is at or near the cellular scale.

In one embodiment, the wire is patterned onto the polymer matrix material as aforesaid, and then incorporated into a medical implant device, including e.g. by wrapping or coating the patterned polymers onto a surface of such a device. In one practice, the wire is patterned onto the polymer matrix material which is then over-coated with the same or a different polymer(s) thus effectively embedding the patterned wire into the resultant polymer matrix material. Over-coating can be by methods known in the art including, e.g. spin coating, spray coating, vapor deposition, and the like. Preferably, the patterned wire is provided with means known in the art to connect to an electrical current for the energetic activation herein contemplated. This includes, e.g. external power sources or configurations that subject the embedded wires to an electromagnetic field effective to create current in same, for example, the patterned wire can be connected through leads; in the case of a catheter, e.g., access can be through the hub port. Alternatively or in combination, an electromagnetic field can be inductively coupled thereby providing the required energy. In those embodiments where the implant device is comprised of a polymer matrix material, the over-coat may be comprised of the same or of a different polymer matrix material.

Figure 2:
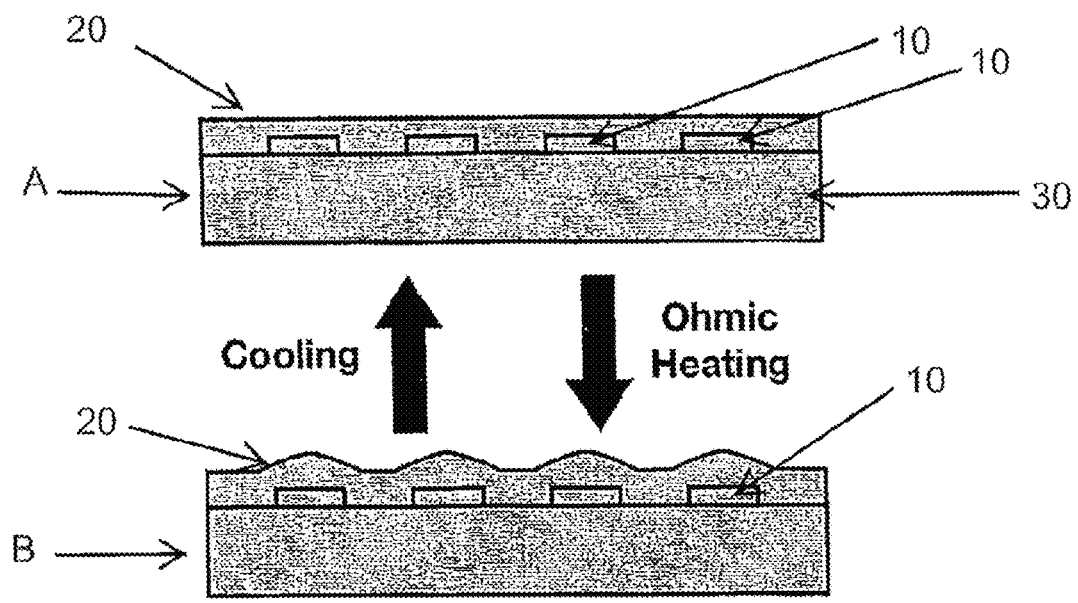
FIG. 2 depicts a cross-section of the embodiment in FIG. 1 showing a practice of thermal actuation whereby a rapid conversion of electrical energy into thermal energy is used to actively modulate the over-coated polymer material of FIG. 1 via cycled ohmic heating and cooling (shown by arrows), the resulting mechanical motion being effective to obstruct biofouling such as protein adsorption and cellular attachment.

In another embodiment, the invention is to a method of treating biofouling, including without limitation, in that of a medical implant device. In one practice in this regard, the implant device is in situ in a patient, and the method can be practiced without removal of the implant. In another practice, the device is external to a patient, the method being performed prior to implant or after removal. In one practice, the patterned wire is connected to a small external power supply, such as a battery pack or electrical transformer, operated effective to thermally actuate at least a portion of the surface of the polymer matrix material within which the wire is patterned. Energetic activation as used herein includes without limitation, thermal actuation which comprises physical changes in surface structure of the polymer matrix material, including changes in chemical characteristics, topography and/or elasticity of the surface, including localized mechanical motion of the surface. Without limitation, energetic activation, such as thermal actuation, results from a time-varying electrical current, a pulse (energy) varying electrical current, or a combination thereof, from the power supply or the like to the patterned wire. In one practice, thermal actuation causes localized temperature changes resulting in thermal expansion and changes in elasticity that are associated with the thermal softening of the polymer matrix material, such as the over-coated material. The local changes in surface properties are sufficient to disrupt the adsorption of fouling agents such as pathogenic microorganisms by e.g. resisting colonization on the surface by same and the disruption of biofilms that may form or be present. In a preferred practice, the power supplied to the patterned wire is cycled effective to produce dynamic changes that vary over time in the polymer surface; for example, the cycling is such as to produce rapid, local fluctuations in temperature, heating and cooling that are transduced to topographic, electrical or chemical changes. FIG. 2 shows an embodiment of this practice. FIG. 2 is a cross-section of the embodiment in FIG. 1. Patterned wire 10 is embedded into polymer matrix material 30 by virtue of over-coat 20. As power is cycled through the patterned wire heater, a rapid conversion of electrical energy to thermal energy takes place causing the surface of over-coat 20 to modulate between state A, wherein the surface of 20 is substantially flat, to state B, wherein the surface 20 has expanded locally situate to the patterned, embedded wire. This fluctuation between A and B, as between states of cooling (A) and ohmic heating (B), is effective to resist biofouling such as protein adsorption and cellular attachment.

The foregoing description and embodiments are not limiting to the scope of the invention. Those skilled in the art will readily appreciate various modifications and changes, all of which are within the scope of the invention.

What is claimed is:

1. A composite comprising:
a matrix phase; and
a single continuous patterned wire having a length in the centimeter range and completely embedded within the matrix phase and having a periodicity at the sub-cellular scale, wherein the single continuous patterned wire is energetically activatable to cause a physical change in the matrix phase effective to treat fouling of the composite, wherein the physical change comprises mechanical motion.

2. The composite of claim 1 wherein the matrix phase comprises a polymer.

3. The composite of claim 2 wherein the polymer is selected from the group consisting of a fluoropolymer, a polycarbonate-based polyurethane, a polyether-based polyurethane, a polyester-based polyurethane, nylon, a nylon block copolymer; high-density polyethylene (HDPE), and combinations thereof.

4. The composite of claim 2 wherein the polymer is selected from the group consisting of a polyester, a polyurethane, a polyamide, a polyamide block copolymer, a polyolefin, a silicone; a latex; a polyvinyl chloride, a polyimide, a polyetheretherketone, and combinations thereof.

5. The composite of claim 1 wherein the composite is a catheter, shunt, artificial joint, dental implant, or cosmetic implant.

6. The composite of claim 1 wherein said single continuous patterned wire is composed of a metal selected from the group consisting of gold, silver, copper, iron, palladium, platinum, carbon, and conducting organic polymers, and combinations thereof.

7. The composite of claim 1 wherein said single continuous patterned wire is lithographically defined.

8. The composite of claim 1 wherein the composite is a laminate and said single continuous patterned wire is present in an insert geometry or a sheet geometry.

9. The composite of claim 1 wherein said single continuous patterned wire is activated by time-varying electrical current, pulse-varying electrical current, or combination thereof.

10. The composite of claim 1 wherein said single continuous patterned wire has a sinuous pattern.

11. The composite of claim 1 wherein said periodicity is about 10 microns or less.

12. The composite of claim 1 wherein said periodicity is about 10 microns.

13. The composite of claim 1 wherein said single continuous patterned wire is composed of a metal selected from the group consisting of gold, silver, palladium, and platinum.

14. The composite of claim 1 wherein said single continuous patterned wire is composed of a metal selected from the group consisting of gold, silver, palladium, and platinum, and wherein the matrix phase is a polyurethane polymer.

15. A medical implant device comprising the composite of claim 1.

16. The medical implant device of claim 15 wherein said device is a catheter, shunt, artificial joint, dental implant, or cosmetic implant.

17. A composite comprising:
a matrix phase; and
a single continuous patterned wire having a length in the centimeter range and completely embedded within the matrix phase and having a periodicity at the sub-cellular scale of about 10 microns or less, wherein the single continuous patterned wire is energetically activatable to cause a physical change in the matrix phase effective to treat fouling of the composite.

* * * * *